United States Patent
Boillot et al.

(10) Patent No.: US 8,411,034 B2
(45) Date of Patent: Apr. 2, 2013

(54) STERILE NETWORKED INTERFACE FOR MEDICAL SYSTEMS

(76) Inventors: Marc Boillot, Plantation, FL (US); Martin Roche, Fort Lauderdale, FL (US)

( * ) Notice: Subject to any disclaimer, the term of this patent is extended or adjusted under 35 U.S.C. 154(b) by 225 days.

(21) Appl. No.: 12/723,486

(22) Filed: Mar. 12, 2010

(65) Prior Publication Data

US 2010/0231509 A1 Sep. 16, 2010

Related U.S. Application Data

(60) Provisional application No. 61/159,793, filed on Mar. 12, 2009.

(51) Int. Cl.
*G06F 3/03384* (2006.01)
(52) U.S. Cl. ........................................ 345/158; 600/300
(58) Field of Classification Search .......... 345/156–184; 359/1–35; 353/42; 600/300–595; 128/906, 128/920–925
See application file for complete search history.

(56) References Cited

U.S. PATENT DOCUMENTS

| | | | |
|---|---|---|---|
| 7,676,356 B2 | 3/2010 | Carmel | |
| 7,676,381 B2 | 3/2010 | Kawakami et al. | |
| 7,676,483 B2 | 3/2010 | Klug | |
| 7,725,162 B2 * | 5/2010 | Malackowski et al. | 600/424 |
| 2003/0163038 A1 * | 8/2003 | Simon et al. | 600/425 |
| 2004/0106916 A1 * | 6/2004 | Quaid et al. | 606/1 |
| 2007/0120834 A1 * | 5/2007 | Boillot | 345/173 |
| 2007/0121097 A1 * | 5/2007 | Boillot | 356/28 |
| 2007/0211031 A1 * | 9/2007 | Marc | 345/163 |
| 2008/0058836 A1 * | 3/2008 | Moll et al. | 606/130 |
| 2008/0059915 A1 * | 3/2008 | Boillot | 715/863 |
| 2008/0312529 A1 * | 12/2008 | Amiot et al. | 600/426 |
| 2010/0013767 A1 * | 1/2010 | Gu et al. | 345/158 |
| 2012/0053597 A1 * | 3/2012 | Anvari et al. | 606/130 |

* cited by examiner

*Primary Examiner* — Liliana Cerullo
(74) *Attorney, Agent, or Firm* — Marc Boillot

(57) ABSTRACT

One embodiment of a sterile networked interface system is provided comprising a hand-held surgical tool and a data processing system. The surgical tool includes a sensor for sensing a physical variable related to the surgery, a wireless communication unit to transmit the physical variable to the data processing system, and a battery for powering the hand-held surgical tool. The surgical tool sends the physical variable and orientation information responsive to a touchless gesture control and predetermined orientation of the surgical tool. Other embodiments are disclosed.

10 Claims, 6 Drawing Sheets

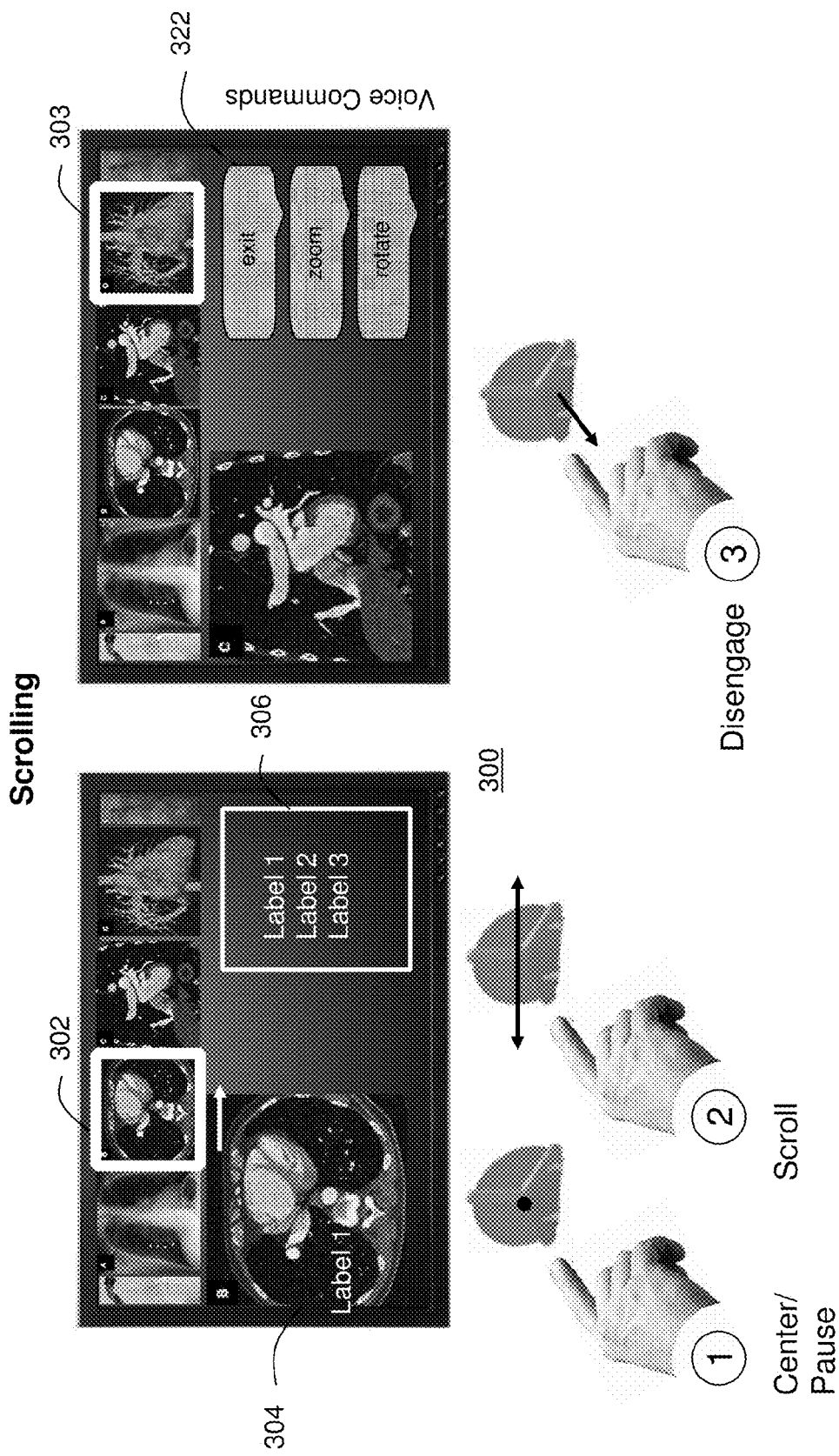

STERILE NETWORKED INTERFACE FOR MEDICAL SYSTEMS

CROSS-REFERENCE TO RELATED APPLICATION

This application claims the priority benefit of U.S. Provisional Patent Application No. 61/159,793 filed Mar. 12, 2009, the entire contents of which are hereby incorporated by reference.

FIELD

The present embodiments of the invention generally relate to the field of hospital systems, more particularly medical device data processing and control.

BACKGROUND

As data becomes more readily available in hospitals and clinics, doctors and patients have more information to process. Computer systems and medical devices provide an interface which allows them to retrieve, interpret and display the information. In the operating room environment, computer systems are generally outside the surgical field and operated by a technician. Electronic surgical tools are providing the surgeon with new means for performing surgery. Although the medical devices may communicate with the computer system there still lacks an intuitive user interface which allows the surgeon to retrieve information.

BRIEF DESCRIPTION OF THE DRAWINGS

The features of the embodiments of the invention, which are believed to be novel, are set forth with particularity in the appended claims. Embodiments of the invention, together with further objects and advantages thereof, may best be understood by reference to the following description, taken in conjunction with the accompanying drawings, in the several figures of which like reference numerals identify like elements, and in which:

FIG. 3A is an exemplary depiction for touchless user interface scrolling according to one embodiment;

DETAILED DESCRIPTION

Figure 1A:
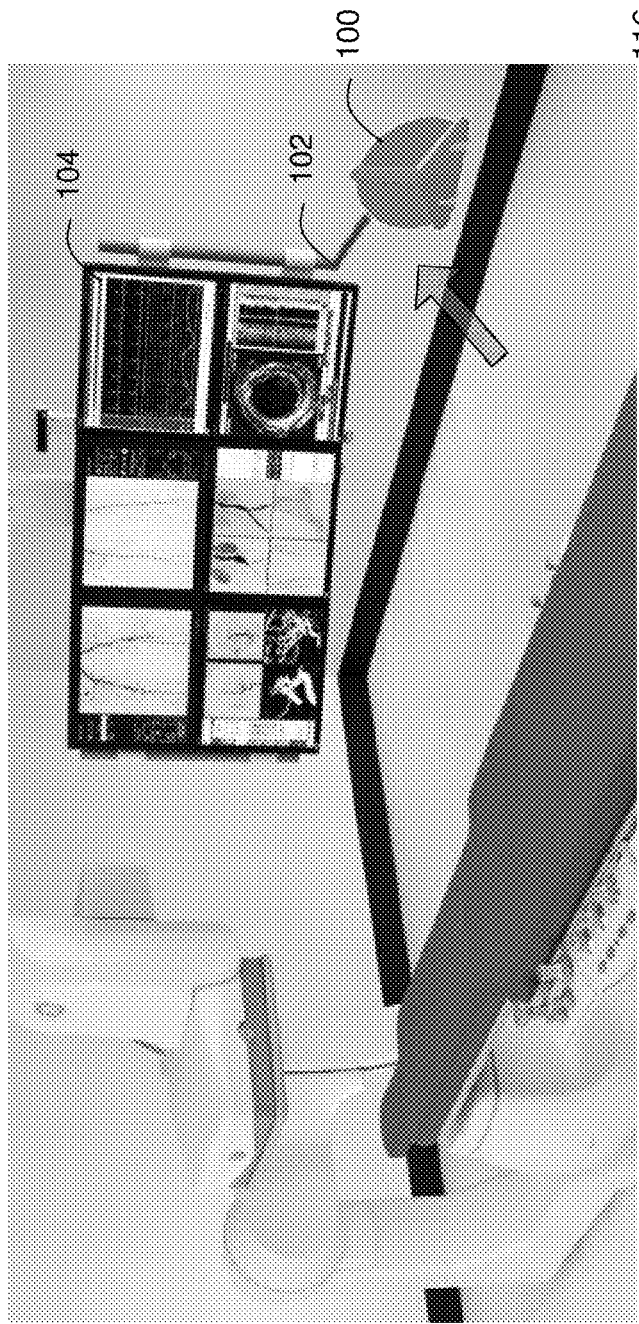
FIG. 1A is an exemplary illustration of an operating room system configured for touchless user interface control according to one embodiment.

While the specification concludes with claims defining the features of the invention that are regarded as novel, it is believed that the invention will be better understood from a consideration of the following description in conjunction with the drawing figures, in which like reference numerals are carried forward.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The terms program, software application, and the like as used herein, are defined as a sequence of instructions designed for execution on a computer system. A program, computer program, or software application may include a subroutine, a function, a procedure, an object method, an object implementation, an executable application, a source code, an object code, a shared library/dynamic load library and/or other sequence of instructions designed for execution on a computer system or embedded electronic device.

FIG. 1A shows an exemplary sterile networked interface in an operating room environment comprising a touchless sensing device 100 and a data processing system 104 display. The sensing device 100 permits the surgeon a sterile user interface for interacting and viewing operational data, processing medical information, and viewing surgical tool functionality. It may be positioned 1-2 feet within reach. It can also be placed farther out of the sterile field. As will be described ahead, the touchless sensing device 100 in various embodiments permits the surgeon the ability to scroll, select, rotate and save data via touchless gestures, and in certain embodiments, update operational tool parameters in accordance with a predetermined work flow. Although shown as a separate unit, the touchless sensing device 100 can be configured peripheral to the display or positioned above. One example of an arrangement is disclosed in U.S. patent application Ser. No. 11/683,416. The touchless sensing device 100 can comprise infrared sensors, ultrasonic sensors, camera elements or a combination thereof as therein specified.

Figure 1B:
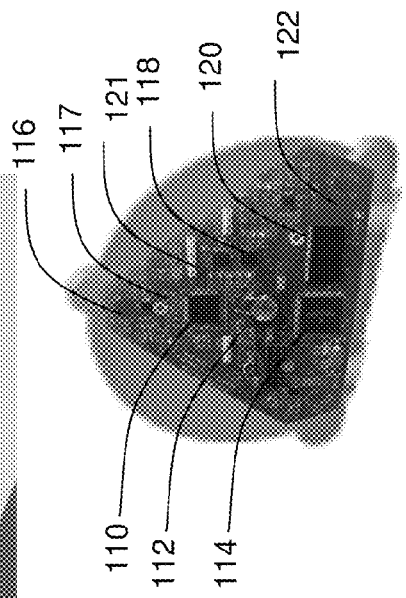
FIG. 1B is an exemplary illustration of a sensory device for processing touchless movements and gesture control according to one embodiment.
Figure 1C:
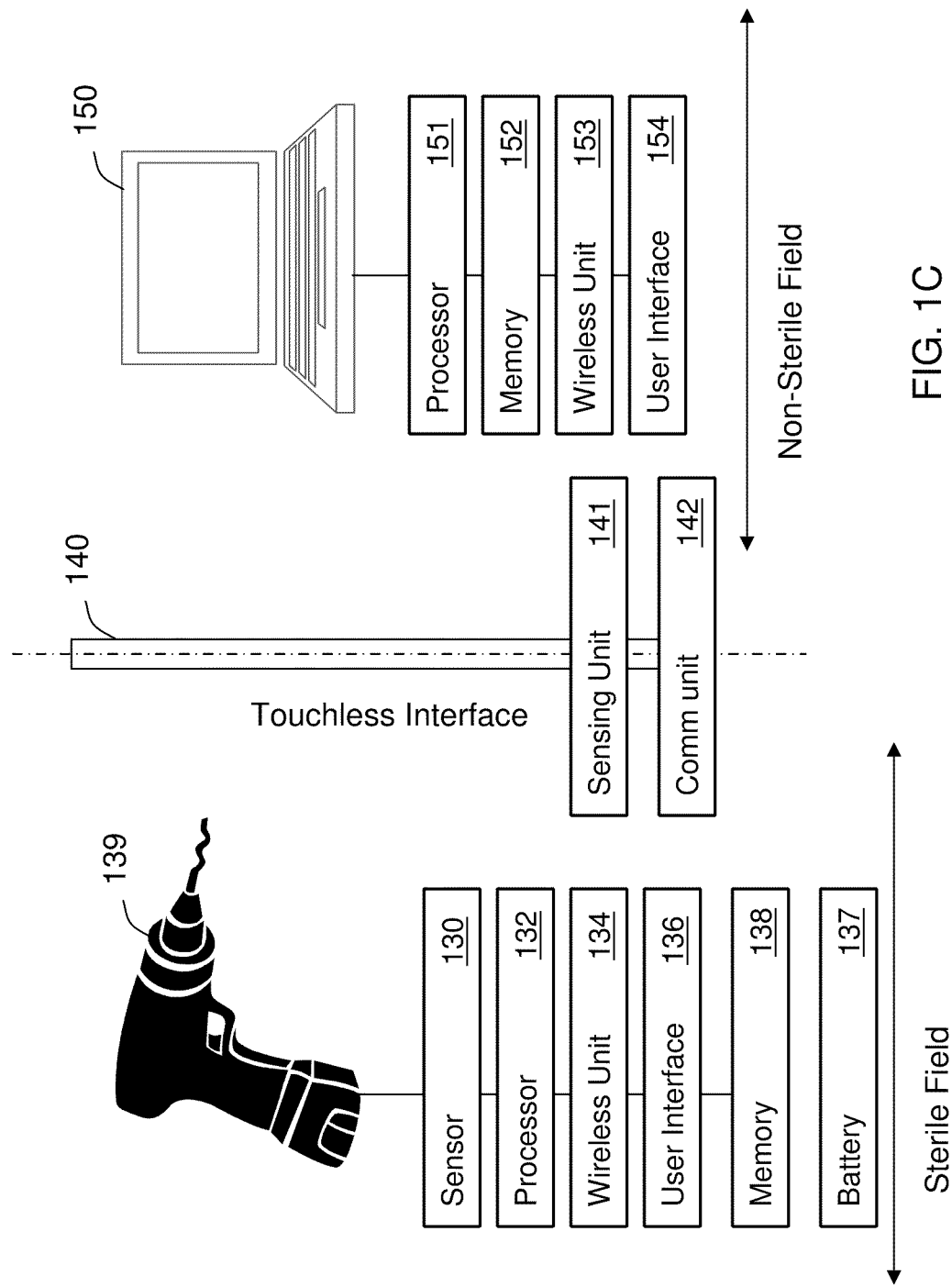
FIG. 1C is an exemplary illustration of a sterile networked interface system according to one embodiment.

FIG. 1B is an exemplary illustration of the components of the touchless sensing device 100 according to one embodiment. The sensing device 100 can include a transmitter 112, three or more receivers 122 (at the corners), a Digital Signal Processor (DSP) 110 to process sensory information from the receivers 122, a communications module (e.g., BlueTooth, ZigBee, or other IEEE protocol), a memory 120, and one or more analog to digital converters and digital to analog converters 118.

Operation of the touchless sensing unit in various configurations for achieving touchless sensing are disclosed in the following U.S. patent application Ser. Nos. 11/559,295; 11/559,325; 11/562,404; 12/146,445.

The touchless sensing device 100 in the configuration shown includes an optical camera element 117 to image an anatomical feature in the sterile field, an ultrasonic transducer 112 to measure a distance to the anatomical feature that is associated with the physical variable, and an accelerometer 121 for identifying an axial tilt and movement. This information can be used by the data processing system in accordance with touchless user input to report proper use and orientation of the surgical tool. As one example, the processor configures one or more of its operational parameters responsive to analyzing the anatomical feature of interest and determining a proper working angle from the orientation.

FIG. 10 is a diagrammatic illustration of an exemplary sterile networked interface system. The sterile networked interface system comprises a hand-held surgical tool 139 used within a sterile field during surgery, a touchless interface 140, and a data processing system 104 outside the sterile field and wirelessly coupled to the surgical tool. The surgical tool comprises a sensor 130 for sensing a physical variable related to the surgery, a wireless communication unit 134 to transmit the physical variable, and a battery 137 for powering the hand-held surgical tool. It is not limited to these features and may include other components of a surgical tool, for example, a processor 132 a user interface 136 and associated memory 138. It can also include a drill, a saw, a rotor, a stator or other mechanical hardware. The data processing system 150 receives the physical variable and orientation information reported from and related to the hand-held surgical tool during the surgery.

The surgical tool 139 communicates a physical variable associated with the surgical procedure to the data processing system 104 responsive to the sensing unit 110 detecting a touchless gesture control and predetermined orientation of the surgical tool 139. The sensing unit 141 (see processor 114 of FIG. 1B) detects touchless gestures of re-centering, accelerated movements, left-right movements, up-down movements, and zoom in and out movements. Touchless finger pointing and hand gestures control aspects of a user interface presented through the data processing system 104. Aspects of touchless sensing are disclosed in issued U.S. Pat. No. 7,620,316.

In another configuration, the hand-held surgical tool 139 includes the touchless sensing device as the user interface component 136 thereon for use within a sterile field during surgery. The hand-held surgical tool 139 comprises the sensor 130 for sensing a physical variable related to the surgery, the wireless communication unit 134 to transmit the physical variable, the battery 137 for powering the hand-held surgical tool. The touchless sensing unit on the hand-held surgical tool identifies a location and movement of a finger or hand gesture, and the processor 132 communicates the physical variable from the hand-held surgical tool 139 to the data processing system 150 responsive to the touchless gesture control and predetermined orientation of the surgical tool. The hand-held surgical tool 139 sends physical variable and orientation information to the data processing system 150 outside the sterile field that is wirelessly coupled to the surgical tool, and that provides operative directives back to the surgical tool for performing a work flow procedure of the surgery based on the physical variable and orientation.

The touchless user interface 150 comprises a sensing unit 141 for identifying a location and movement of a finger or hand gesture; a processor to operate display information for touchless sensing, touchless image scrolling, selection, and saving, touchless gesture controls, and touchless image rotation; and a communications interface 142 for sending the location and movement to a display of the data processing system for controlling a user interface of the hand-held surgical tool. The data processing system 150 can include a processor 151, a memory 152, a wireless unit 153 and user interface 154. The touchless sensing device 100 provides 1) display calibration for touchless sensing, 2) touchless thumbnail Scrolling, 3) touchless gesture controls, 4) touchless image rotation, 5) small vowel recognition vocabulary for enhanced interface control, and 6) pointing to image features with drag & drop labeling.

One aspect of range detection and positioning determination as described below are disclosed in issued U.S. Pat. No. 7,414,705. As one particular example, the sensor comprises a pulse shaper for producing a pulse shaped signal, the pulse shaped signal intended for reflecting off an anatomical feature to produce a reflected signal, wherein at least one portion of the pulse shaped signal is at least one among a frequency modulated region, constant frequency region, phase modulated region, and a chirp region, a phase detector for receiving and identifying a relative phase of the reflected signal with respect to a previously received reflected signal, and a processor operatively coupled to the pulse shaper for receiving the reflected signal, tracking a location and a movement of the hand-held surgical tool from an estimated arrival time of the reflected signal and the relative phase, and providing the physical variable to a user interface control in accordance with the location and the movement of the hand-held surgical tool. The processor estimates the location of the first object from a frequency modulated region of the reflected signal, and a velocity of the first object from the relative phase from a continuous frequency region of the reflected signal and responsive to a touchless gesture control and predetermined orientation of the surgical tool communicates the physical variable from the hand-held surgical tool to the data processing system.

Figure 2B:
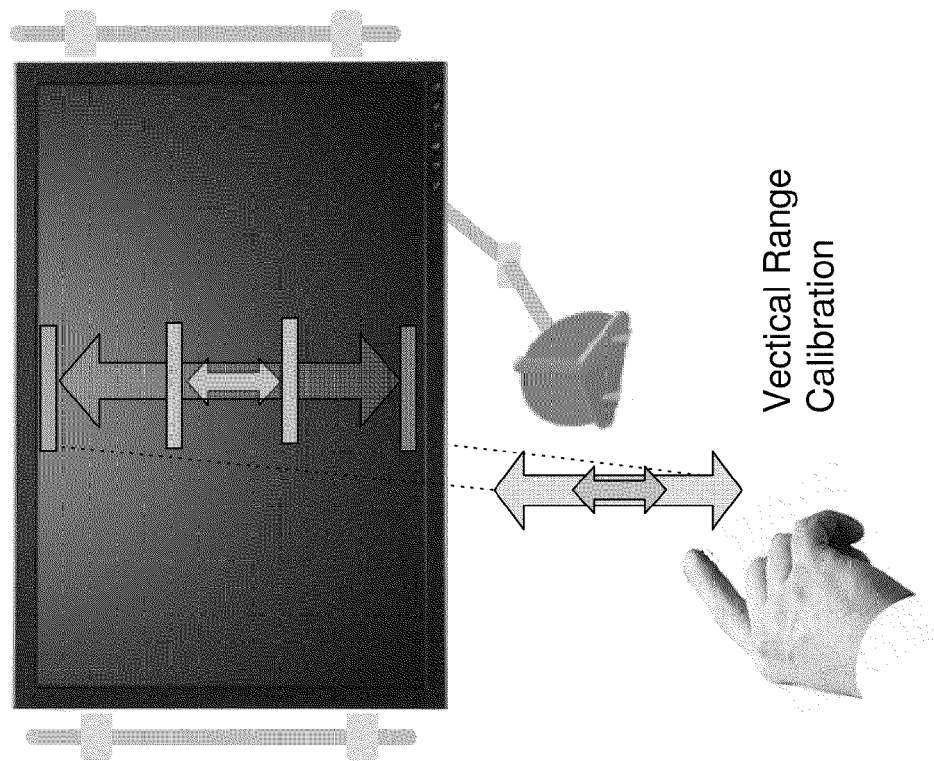
FIGS. 2A and 2B are exemplary illustrations for user interface calibration according to one embodiment.
Figure 2A:
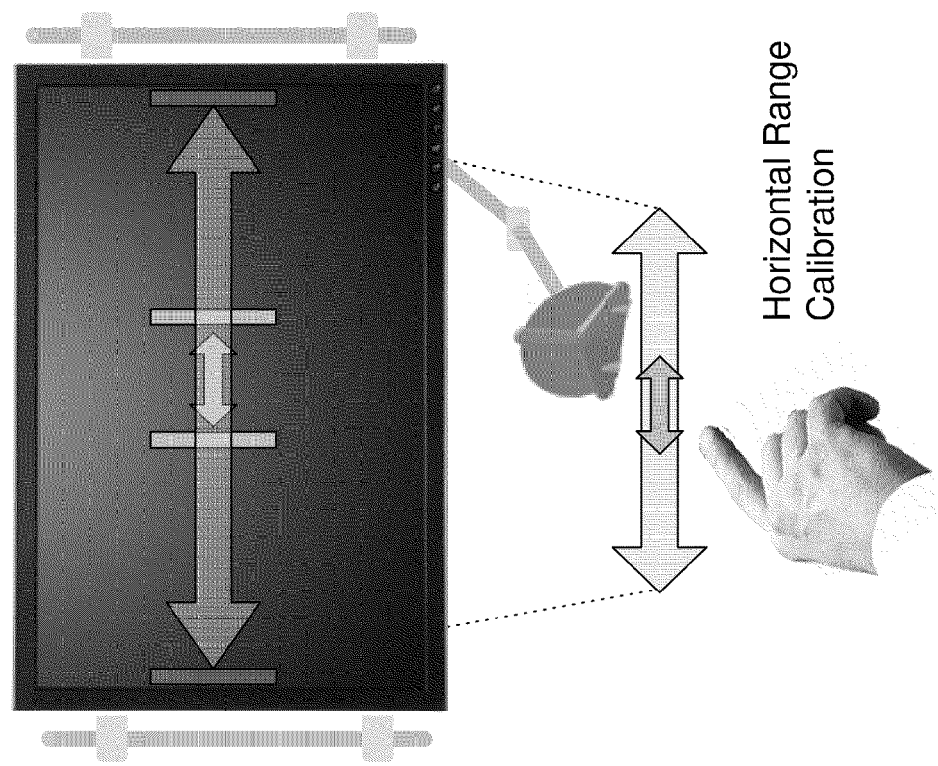

FIGS. 2A and 2B shows exemplary calibration steps for setting up the touchless sensing device 100. The device is calibrated to the display based on the finger range of motion. That is, the dimensions of the touchless sensing space are mapped to the display. For instance, a 6 in left and 6 in right motion (12 inch horizontal span) is mapped to the 30-50 inch wide display range. A 4 in up and 4 in down motion (8 inch vertical span) is mapped to the 20-30 inch display height since screen is rectangular and vertical arm movement may require more lifting (fatiguing) motion. The touchless sensing device 100 can also be used in conjunction with a hand-held device such as a wireless pointer in addition to the previously shown hand-held drill. As illustrated the surgeon pauses finger/hand, then moves finger/hand left and right for desired full range of arm/hand motion. Sensors can also be included in a surgical glove to provide further gesture functionality. The dual bars open during the jitter motion to visually identify the mapped horizontal boundaries. Similarly during height calibration dual bars are shown opening during a left-right jitter motion to visually identify a mapped horizontal boundaries.

In another embodiment, the touchless sensing unit can be configured for touchless interface control and range detection. In either configuration the sensor identifies a location and movement of a finger or hand gesture, and the communications interface sends the location and movement to a display device of the data processing system for controlling one or more parameters of the surgical tool 139 by way of the touchless user interface 150. The touchless sensing unit communicates a physical variable captured during a surgical procedure from the surgical tool to the data processing system for presentation in the display responsive to a touchless gesture control and predetermined orientation of the surgical tool. As one example, the user pauses the surgical tool 139 at a certain angle and with the other hand points to the screen. The accelerometer identifies an axial tilt and movement. The processor references the orientation of the hand-held surgical tool with respect to a coordinate system established by the anatomical feature position, tilt and movement. The interface isolates and displays a point of interest, for example, an anatomical feature of the patient according to an orientation of the surgical tool. The surgical tool can capture an image of and a distance to the anatomical feature which is reported on the display. Surgical feedback provided via the touchless user interface can then be used to set one or more parameters of the surgical tool 139 for updating the work flow. The sensor can be operatively coupled to the surgical tool. In another embodiment the sensor is operatively coupled to the data processing system apart from the tool. As another example, the processor 114 references the orientation of a hand-held surgical tool with respect to the anatomical feature, distance, tilt and movement. The data processing system 150 provides operative directives to the surgical tool in accordance with a predetermined work flow that takes into account the physical variable.

FIGS. 3A and 3B shows a thumbnail scrolling user interface on the screen 300. The screen can include a variable or fixed number of thumbnail images 302 on the top row. To refresh more images, surgeon can re-center (1) the finger once its pointed to the far left or right of reach. As another example, the system can have 10 thumbnail images 302 in a buffer, but only show 5 at a time, where the entire 10 images are mapped to the surgeon's full horizontal hand motion to permit scrolling of the 10 images. The active image (the one pointed too) can have a colored box outline for example. That image can be actively displayed in the lower left corner 304 as the surgeon fingers across (scrolls 2) thumbnail images. The surgeon can disengage (3) via retracted finger movement or voice command.

One example method of thumbnail scrolling five (5) thumbnail images fixed on the display, includes method steps where the surgeon raises and centers finger/hand and pauses for a brief moment (e.g., 1 second) in front of the touchless sensing device 100 to indicate readiness, a border 302 will be displayed indicating touchless control acquired. The surgeon moves their finger/hand left or right to scroll through images. An actively selected image will be outlined by border box and will enlarge in (e.g., left main) display area. The surgeon retracts finger/hand to disengage touchless control, which leaves active image enlarged. Alternatively, surgeon can say a word to disengage (exit) touchless control via voice recognition applications. One example of voice recognition combined with touchless sensing is disclosed in U.S. patent application Ser. No. 12/120,654.

Figures 4A, 4B:
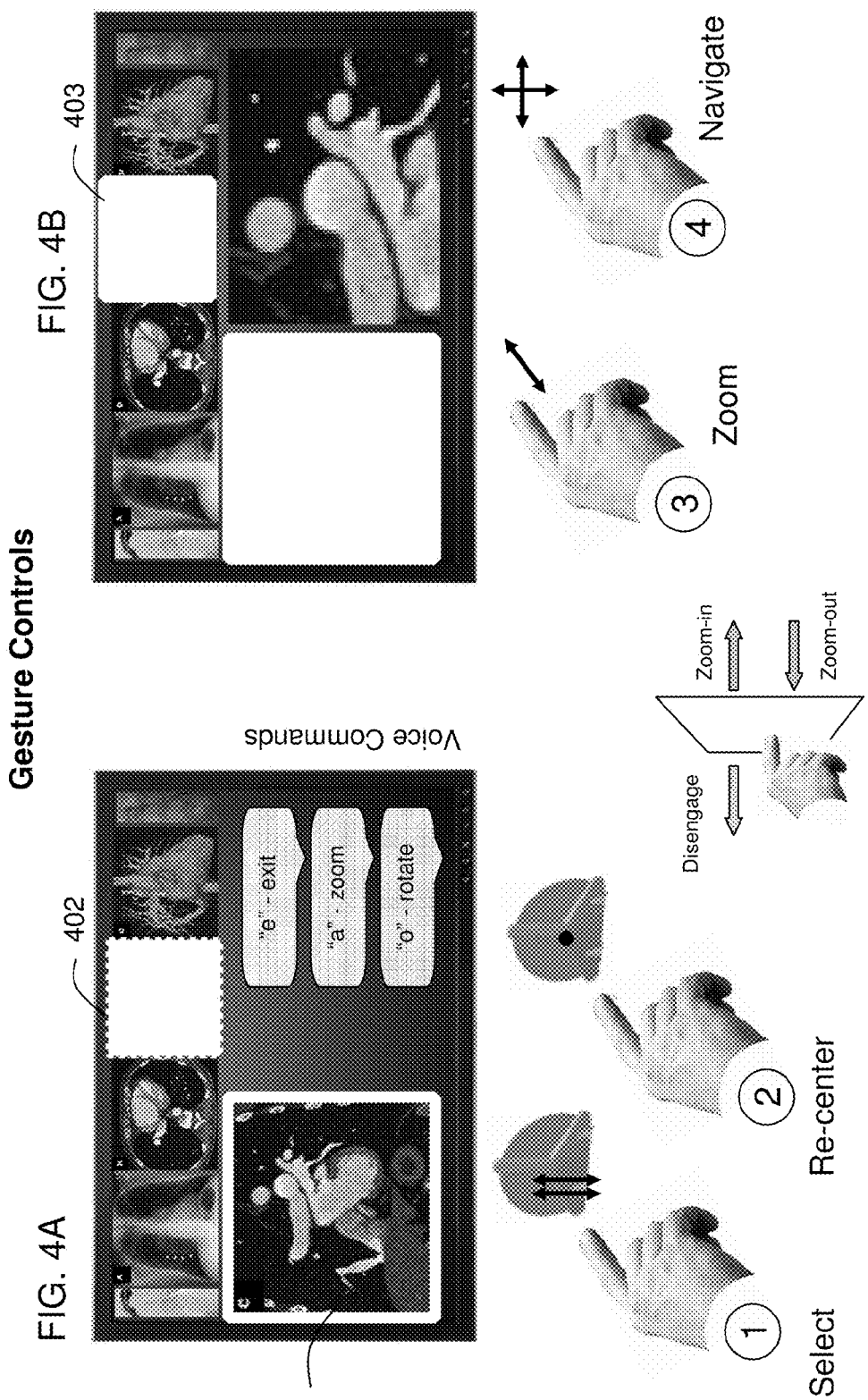
FIGS. 4A and 4B are exemplary depictions for touchless user interface gesture controls according to one embodiment.

FIGS. 4A and 4B show exemplary touchless gesture controls for the user interface on the screen 400. To select an image the surgeon can perform a brief up/down (~1 inch) finger motion. In an alternate configuration, the surgeon can do brief right->re-center movements to scroll to the right, and left->re-center movements to scroll left, so the hand can remain sufficiently centered. A simple voice command can be used to start touchless gesture controls, to override touchless control for image thumbnail scrolling as shown. The 3D location at which the surgeon re-centers the finger-hand can establish the reference zoom plane. The surgeon can slowly move the finger forward (in) to zoom in. Then, the surgeon can slowly move finger back to zoom-out back to the reference zoom plane.

One example method of gesture control comprises steps where the surgeon jitters the finger/hand up and down to select the image. The thumbnail border turns green and flashes to indicate a waiting state. The surgeon then re-centers and pauses the finger/hand in front of touchless sensing device 100 to acquire gesture control (e.g., thumbnail border then stops flashing and turns solid green indicating ready) Re-centering is also the motion required if the surgeon previously disengaged iPoint control. As one example, the surgeon speaks a voice command to start touchless navigation/zoom, and can then move up/down/left/right to navigate image in conjunction with inward pointing movement to zoom-in on image. (Zoom-out is permitted after zoom-in).

Means for operation of the touchless sensing unit for gesture control and user interfaces are disclosed in the following U.S. patent applications, all of which are hereby incorporated by reference in their entirety: Ser. Nos. 11/562,413; 11/566,137; 11/566,148; 11/566,156; 11/683,410; 11/683,412; 11/683,413; 11/683,415 and 11/683,416.

An accelerated retracting finger movement (or voice command) can disable (exit) touchless control thereby temporarily locking the image at the zoom-level and position just prior to the accelerated retracted finger movement. This releases touchless control and permits the surgeon to continue the medical procedure. In order to enable and re-engage touchless control, the surgeon can center and pause the finger/hand in front of the iPoint again. A thumb motion on the same hand an also be performed for control (an action similar to mimicking a thumb trigger). The 3D location at which the surgeon re-centers the finger-hand establishes the reference zoom plane. The surgeon can slowly move the finger forward (in) to zoom in. Then, the surgeon can slowly move finger back to zoom-out back to the reference zoom plane.

An accelerated retracting finger movement can disable touchless control thereby temporarily locking the image at the zoom-level and position just prior to the accelerated retracted finger movement. This releases touchless control and permits the surgeon to continue the medical procedure. A thumb motion on the same hand can alternatively signal the image lock instead of the accelerated retracting movement). To enable and re-engage touchless control, the surgeon can center and pause the finger/hand in front of the sensing device 100 again. Voice commands can also be used in conjunction with drag and drop labeling. The surgeon can select labels from a user interface 306 which can then be dragged to anatomical features on the image 304.

Figure 5:
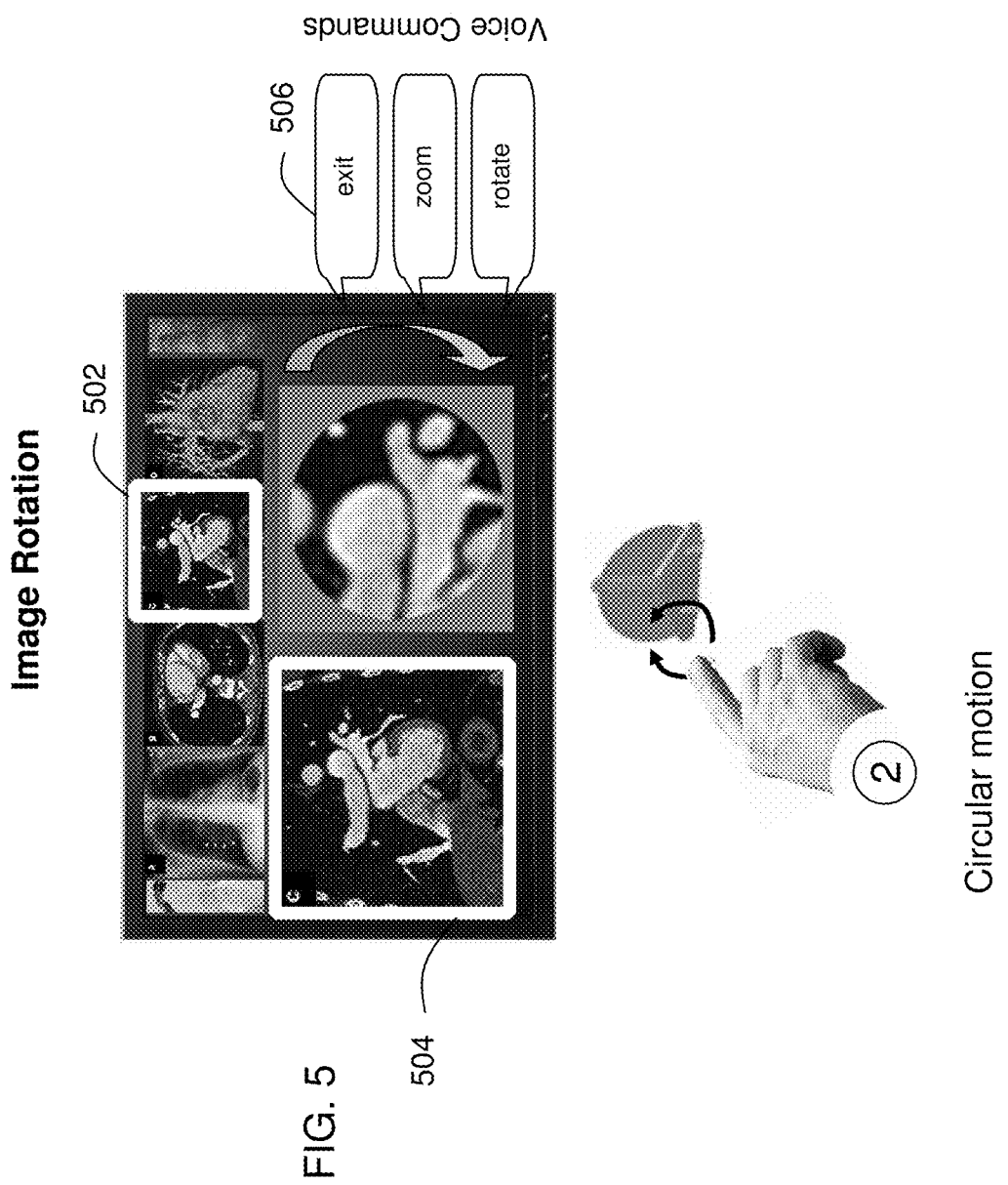
FIG. 5 is an exemplary depiction for touchless user interface image analysis and feedback according to one embodiment.

FIG. 5 shows an exemplary touchless user interface application for image rotation. Upon selecting an image 502, then displayed in a larger window 504, the surgeon can speak a voice command 506 such as "rotate", to commence touchless rotation controls. The surgeon can then perform touchless clockwise and counter clockwise finger motions to rotate the image. The touchless sensing device 100 translates the finger motions to image translations that rotate the image. The ipoint can identify a finger (or hand) pause to stop rotation and lock to the current rotation to permit surgeon to retract hand. Rotation controls include voice recognition, circular finger motions, and forward and retracting hand motions.

Means for operation of the touchless sensing unit to detect scrolling, gestures and rotations for controlling user interfaces are disclosed in the following U.S. patent applications, all of which are hereby incorporated by reference in their entirety: Ser. Nos. 11/839,323; 11/844,329; 11/850,634; 11/850,637; 11/930,014; 11/936,777; 11/936,778; 12/050,790; 12/099,662 and 12/120,654

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A sterile networked interface system comprising
a hand-held surgical tool used within a sterile field during surgery, the surgical tool comprising:
    a sensor for sensing a physical variable related to the surgery;
    a wireless communication unit to transmit the physical variable; and
    a battery for powering the hand-held surgical tool;
a data processing system including a display, the data processing system located outside the sterile field and wirelessly coupled to the surgical tool for receiving the physical variable and orientation information reported from and related to the hand-held surgical tool during the surgery; and
a touchless interface comprising:
    a sensing unit with a transmitter, three or more receivers, a processor, a communications interface, and a memory included thereon,
where the touchless interface creates a touchless sensing space in front of the sensing unit with dimensions mapped to the display; and where the touchless interface communicates the physical variable from the hand-held surgical tool to the data processing system for presentation of an image related to the physical feature in the display, responsive to a touchless gesture control detected within the touchless sensing space and a predetermined orientation of the surgical tool.

2. The sterile networked interface of claim 1 where the touchless user interface comprises:
    the sensing unit for identifying a location and movement of a finger or hand gesture; the processor to operate display information for:
    touchless sensing,
    touchless image scrolling, selection, and saving;
    touchless gesture controls, and
    touchless image rotation; and
    the communications interface for sending the location and movement to the display of the data processing system for controlling a user interface of the hand-held surgical tool.

3. The sterile networked interface of claim 2, where the processor detects touchless gestures of re-centering, accelerated movements, left-right movements, up-down movements, and zoom in and out movements.

4. The sterile networked interface of claim 1 where the sensor includes
    an optical camera element to image an anatomical feature in the sterile field;
    an ultrasonic transducer to measure a distance to the anatomical feature that is associated with the physical variable;
    and, an accelerometer for identifying an axial tilt and movement;
where the processor references the orientation of the hand-held surgical tool with respect to the anatomical feature, distance, tilt and movement.

5. The sterile networked interface of claim 3 where the data processing system provides operative directives to the surgical tool in accordance with a predetermined work flow that takes into account the physical variable.

6. The sterile network interface of claim 1, where the display of the data processing system during width calibration shows dual bars open during a left-right jitter motion to visually identify a mapped horizontal boundaries, and during height calibration shows dual bars open during an up-down jitter motion to visually identify a mapped vertical boundaries.

7. A system configurable for touchless interface control and range detection, the system comprising:
    a sensor operatively coupled to a surgical tool to report a position and orientation of the surgical tool;
    a touchless sensing unit comprising a transmitter, three or more receivers, a processor, a communications interface, and a memory included thereon,
    the touchless sensing unit for creating a touchless sensing space in front of the touchless sensing unit with dimensions mapped to the display;
    the touchless sensing space for identifying a touchless location and movement of a finger or hand gesture;
    the communications interface for sending the location and movement to a display device of a data processing system for controlling one or more displayed parameters of the surgical tool by gestures on the touchless sensing space;
where the touchless sensing unit communicates a physical variable captured during a surgical procedure from the surgical tool to the data processing system for presentation of an image related to the physical variable in the display, responsive to a touchless gesture control in the touchless sensing space of the finger or hand movement and predetermined orientation of the surgical tool.

8. The system of claim 7, where the sensor is operatively coupled to the data processing system.

9. The system of claim 7, comprising
    a wireless communication unit to transmit the physical variable; and
    a battery for powering the hand-held surgical tool.

10. The system of claim 7, where the sensor includes
    an optical camera element to image an anatomical feature in the sterile field;
    an ultrasonic transducer to measure a position of the anatomical feature relative to the hand-held surgical tool that is associated with the physical variable;
    and, an accelerometer for identifying an axial tilt and movement;
where the processor references the orientation of the hand-held surgical tool with respect to a coordinate system established by the anatomical feature position, tilt and movement.

* * * * *